US006902926B1

(12) United States Patent
Ward et al.

(10) Patent No.: US 6,902,926 B1
(45) Date of Patent: Jun. 7, 2005

(54) TOXOPLASMA GONDII APICAL MEMBRANE ANTIGEN-1

(75) Inventors: Gary E. Ward, Essex Junction, VT (US); Carolyn G. Conant, San Francisco, CA (US); Brian Ward, Montreal (CA)

(73) Assignees: University of Vermont and State Agricultural College, Burlington, VT (US); McGill University, Quebec (CA)

( * ) Notice: Subject to any disclaimer, the term of this patent is extended or adjusted under 35 U.S.C. 154(b) by 106 days.

(21) Appl. No.: 10/039,770

(22) Filed: Nov. 9, 2001

Related U.S. Application Data
(60) Provisional application No. 60/247,870, filed on Nov. 9, 2000.

(51) Int. Cl.[7] .............................. C12N 1/10; C12Q 1/68; A61K 39/012; A61K 39/00
(52) U.S. Cl. ........................ 435/258.1; 435/6; 435/69.1; 435/69.7; 536/23.4; 536/23.7; 424/273.1; 424/266.1; 424/265.1; 424/185.1
(58) Field of Search .......................... 424/185.1, 273.1, 424/265.1, 266.1, 258.1; 435/6, 69.1, 69.7, 94.1, 7.2, 7.22, 19.6, 19.01, 19, 264.2, 320.1; 536/23.7, 23.4

(56) References Cited

U.S. PATENT DOCUMENTS

| 5,101,017 A | 3/1992 | Rubinstein et al. |
| 6,066,623 A | 5/2000 | Hoffman et al. |
| 6,120,770 A | 9/2000 | Adams et al. |

OTHER PUBLICATIONS

Rudinger et al, in "Peptide Hormones", edited by Parsons, J.A., University Park Press, Jun. 1976, p. 6).*
Burgess et al., The Journal of Cell Biology, 111:2129–2138, 1990).*
Lazar et al., Molecular and Cellular Biology, 8(3): 1247–1252, 1988.*
Jobling et al. (Mol. Microbiol. 1991, 5(7): 1755–67.*
Ellis, R.W. (Chapter 29 of "VACCINES" Plotkin, 5.A. et al. (eds) published by W. B. Saunders company (Philadelphia) in 1988, especially p. 571.*
Hehl et al, Infection and Immunity, Dec. 2000, p. 7078–7086, vol. 68, No. 12.*
Hehl et al 1997, Acession No.: AF010264.*
Hehl et al Acession No.: O15981, 1998.*
Bercovici, T. et al., "5–[$^{125}$ I]Iodonaphthyl Azide, a Reagent to Determine the Penetration of Proteins into the Lipid Bilayer of Biological Membranes", *Biochemistry*, Apr. 18, 1978, pp. 1484–1489, vol. 17, No. 8.
Brydges, S.D. et al., "Molecular characterization of TgMIC5, a proteolytically processed antigen secreted from the micronemes of *Toxoplasma gondii*", *Molecular and Biochemical Parasitology*, 2000, pp. 51–66, vol. 111, Elsevier Science B.V.

Carey, K.L. et al., "Identification and molecular characterization of GRA8, a novel, proline–rich dense granule protein of *Toxoplasma gondii*", *Molecular and Biochemical Parasitology*, 2000, pp. 25–37, vol. 105, Elsevier Science B.V.
Carruthers, V.B. et al., "Mobilization of intracellular calcium stimulates microneme discharge in *Toxoplasma gondii*", *Molecular Microbiology*, 1999, pp. 421–428, vol. 31, No. 2, Blackwell Science Ltd.
Carruthers, V.B. et al., "Ethanol and acetaldehyde elevate intracellular [$Ca^{2+}$] and stimulate microneme discharge in *Toxoplasma gondii*", *Biochem. J.*, 1999, pp. 379–386, vol. 342, Biochemical Society Great Britain.
Carruthers, V.B. et al., "Secretion of micronemal proteins is associated with toxoplasma invasion of host cells", *Cellular Microbiology*, 1999, pp. 225–235, vol. 1, No. 3, Blackwell Science Ltd.
Carruthers, V.B. et al., "The *Toxoplasma* Adhesive Protein MIC2 is Proteolytically Processed at Multiple Sites by Two Parasite–derived Proteases", *The Journal of Biological Chemistry*, May 12, 2000, pp. 14346–14353, vol. 275, No. 19, The American Society for Biochemistry and Molecular Biology, Inc. USA.
Chittum, H.S. et al., "Rabbit β–Globin is Extended Beyond Its UGA Stop Codon by Multiple Suppressions and Translational Reading Gaps", *Biochemistry*, 1998, pp. 10866–10870, vol. 37, American Chemical Society.
Church, W.R. et al., "Monoclonal Antibodies to the Amino– and Carboxyl–Terminal Domains of Ovotransferrin", *Hybridoma*, Oct. 1988, pp. 471–484, vol. 7, No. 5, Mary Ann Liebert, Inc.
Donahue, C.G. et al., "Characterization of Apical Membrane Antigen–1, AMA–1, a novel transmembrane protein of *Toxoplasma gondii*", Department of Microbiology and Molecular Genetics Annual Retreat Poster, Oct. 15–16, 1999.
Donahue, C.G. et al., "The *Toxoplasma* homolog of *Plasmodium* apical membrane antigen–1 (AMA–1) is a microneme protein secreted in response to elevated intracellular calcium levels", *Molecular Parasitology Meetings Poster*, Woods Hole, MA, Sep. 17–21, 2000.

(Continued)

*Primary Examiner*—Mark Navarro
*Assistant Examiner*—Padma Baskar
(74) *Attorney, Agent, or Firm*—Wolf, Greenfield & Sacks, P.C.

(57) ABSTRACT

The invention provides polypeptide fragments derived from TgAMA-1, nucleic acids that encode the polypeptide fragments, and TgAMA-binding polypeptides such as antibodies. Methods for using the polypeptide and nucleic acid molecules to produce vaccines are also provided. In addition the invention provides methods involving use of the polypeptides, nucleic acids, and binding polypeptides, such as antibodies, for the prevention and treatment of Toxoplasmosis.

9 Claims, No Drawings

OTHER PUBLICATIONS

Donahue, C.G. et al., "The *Toxoplasma* homolog of *Plasmodium* apical membrane antigen–1 (AMA–1) is a microneme protein secreted in response to elevated intracellular calcium levels", *Department of Microbiology and Molecular Genetics Annual Retreat*, Oral Presentation, Oct. 7, 2000.

Donahue, C.G. et al., "The *Toxoplasma* homolog of *Plasmodium* apical membrane antigen–1 (AMA–1) is a microneme protein which is secreted from the parasite in response to elevated intracellular calcium levels", *ASCB Annual Meeting Article No. 1236*, San Francisco, CA, Dec. 9–13, 2000, Molecular Biology of the Cell II.

Eng, J.K. et al., "An Approach to Correlate Tandem Mass Spectral Data of Peptides with Amino Acid Sequences in a Protein Database", *J. Am. Soc. Mass. Spectrom*, 1994, pp. 976–989, vol. 5, American Society for Mass Spectrometry.

Hodder, A.N. et al., "The Disulfide Bond Structure of *Plasmodium* Apical Membrane antigen–1", *The Journal of Biological Chemistry*, Nov. 15, 1996, pp. 29446–29452, vol. 271, No. 46, The American Society for Biochemistry and Molecular Biology, Inc. USA.

Roos, D.S. et al., "Chapter 3: Molecular Tools for Genetic Dissection of the Protozoan Parasite *Toxoplasma gondii*", *Methods in Cell Biology*, 1994, pp. 27–63, vol. 45, Academic Press, Inc.

Wan, K.L. et al., "Molecular characterisation of an expressed sequence tag locus of *Toxoplasma gondii* encoding the microneme protein MIC2", *Molecular and Biochemical Parasitology*, 1997, pp. 203–214, vol. 84, Elsevier Science B.V.

Ward, G.E. et al., "96–Well plates providing high optical resolution for high–throughput, immunofluorescence–based screening of monoclonal antibodies against *Toxoplasma gondii*", *Journal of Immunological Methods*, 1999, pp. 11–18, vol. 230, Elsevier Science B.V.

* cited by examiner

TOXOPLASMA GONDII APICAL MEMBRANE ANTIGEN-1

RELATED APPLICATIONS

This application claims priority under 35 U.S.C. §119 to U.S. 60/247,870, filed Nov. 9, 2000, the entire contents of which is hereby incorporated by reference.

Government Support

This invention was made in part with government support under grant number R29A 142355 from the National Institutes of Health (NIH). The government may have certain rights in this invention.

FIELD OF THE INVENTION

The present invention relates to TgAMA-1, and TgAMA-1-based animal and human vaccines for toxoplasmosis.

BACKGROUND OF THE INVENTION

Toxoplasmosis is among the most common parasitic diseases of man. Serosurveys suggest prevalence rates as high as 70–90% in many areas of both the developing and developed world. Between 10–45% of Americans become infected at some point in their lives. An infection in an individual with a competent immune system generally has minor or no symptoms. The infection tends to be self-limiting, with the individual's immune system controlling and eliminating most of the parasites. Some parasites remain in bradyzoite form following acute infection and will be present in cysts in the central nervous system and muscle throughout the remainder of the individual's life.

In contrast to the mild clinical symptoms of infection seen in a healthy individual with an intact immune system, subjects with weakened or otherwise compromised immune systems can have serious clinical effects from toxoplasma infection. In the fetus, toxoplasma infection can cause mental retardation, visual defects, and death. Toxoplasma infection can cause neurological damage, ocular lesions and death in adults with compromised immune systems, a group which includes for example individuals with HIV infection or patients undergoing immune-suppressive treatment for cancer.

Acute toxoplasmosis can be difficult to treat. Sulfadiazine/pyramethamine is a regimen of choice, although side effects serious enough to warrant discontinuation of treatment are common. The toxic and potentially teratogenic effects of this regimen make management of the pregnant woman particularly problematic. AIDS patients require lifelong suppressive therapy to prevent relapse, and a many as one third of the patients receiving suppressive sulfadiazine/pyrimethamine therapy cannot tolerate the adverse side effects. For those who can tolerate the drugs, relapse occurs frequently. Pyrimethamine/clindamycin is a useful alternative therapy in AIDS patients who suffer an unusually high frequency of side effects from sulfa drugs. Unfortunately, this alternative combination can also cause considerable toxicity and is less effective at preventing relapse. Prevention of transmission through vaccination would be preferable to treatment, particularly for pregnant women and the immunocompromised.

SUMMARY OF THE INVENTION

According to one aspect of the invention, isolated TgAMA-1 polypeptide molecules are provided. The TgAMA-1 polypeptide molecules include antigenic fragments of the polypeptide sequence set forth as amino acids SEQ ID NO: 1.

According to another aspect of the invention, fusion proteins are provided that include the foregoing antigenic polypeptide.

According to another aspect of the invention, isolated TgAMA-1 nucleic acid molecules are provided. The TgAMA-1 nucleic acid molecules are selected from the group consisting of a fragment of the nucleotide sequence set forth as nucleotides 1–2507 of SEQ ID NO: 2 between 12 and 2506 nucleotides in length, and complements of (a), wherein the fragment encodes the foregoing isolated TgAMA-1 polypeptide.

According to another aspect of the invention, expression vectors are provided and include the isolated foregoing TgAMA-1 nucleic acid molecule operably linked to a promoter.

According to another aspect of the invention, expression vectors are provided and include an isolated nucleic acid molecule of SEQ ID NO: 2 operably linked to a promoter.

According to another aspect of the invention, host cells transformed or transfected with the aforementioned expression vectors are provided. In some embodiments, the host cell is an insect cell. In certain embodiments, the insect cell is a High Five™ cell.

According to another aspect of the invention, a transgenic non-human animal that includes the foregoing expression vector are provided. In some embodiments, the transgenic non-human animal expresses a variable level of TgAMA-1. In certain embodiments, the transgenic non-human animal expresses an antigenic fragment of SEQ ID NO: 1. In some embodiments, the transgenic non-human animal is a mammal. In certain embodiments, the transgenic non-human animal is a bovine.

According to another aspect of the invention vaccine compositions are provided that include the foregoing isolated TgAMA-1 polypeptide and an adjuvant.

According to yet another aspect of the invention, vaccine compositions are provided that include TgAMA-1 or a functionally active variant thereof, and an adjuvant.

In some embodiments of the foregoing vaccine compositions the vaccine is a proteosome vaccine. In certain embodiments of the forgoing vaccine compositions, the adjuvant is selected from the group consisting of: mineral gels, e.g., aluminum hydroxide; surface active substances such as lysolecithin, pluronic polyols; polyanions; peptides; alum, MDP, N-acetyl-muramyl-L-threonyl-D-isoglutamine (thr-MDP), N-acetyl-nor-muramyl-L-analyl-D-isoglutamine, and N-acetylmuramyl-L-alanyl-D-isoglutaminyl-L-analanine-2-(1'-2'dipalmitoyl-sn-glycero-3-hydroxyphosphroyloxy)-ethylamine, monophosphoryl lipid A; saponins (QS21; DQS21); QS-7, QS-17, QS-18, and QS-L1; incomplete Freund's adjuvant; complete Freund's adjuvant; montanide; vitamin E, oil emulsions, and various water-in-oil emulsions prepared from biodegradable oils such as squalene and/or tocopherol.

According to some aspects of the invention, methods for immunizing a subject are provided. The methods include administering to the subject an effective amount for immunizing the subject, of the foregoing vaccines. In some embodiments the subject is a mammal. In certain embodiments the subject is a human. In some embodiments, the subject is at risk of infection from *Toxoplasma gondii*. In some embodiments, the subject is a mammal. In certain embodiments, the subject is a human.

According to another aspect of the invention, TgAMA-1 binding polypeptides that selectively bind to the foregoing isolated TgAMA-1 polypeptide are provided. In some embodiments, the TgAMA-1 binding polypeptide is an antibody or antigen-binding fragment of an antibody. In certain embodiments the antibody or antigen-binding fragment specifically binds to a region comprising about 12 or more cysteine residues of the forgoing isolated TgAMA-1 polypeptide. In certain embodiments, the binding polypeptide blocks entry of Toxoplasma parasite into a cell. In some embodiments, the TgAMA-1 binding polypeptide is a monoclonal antibody. In certain embodiments, the TgAMA-1 binding polypeptide is a humanized monoclonal antibody.

According to another aspect of the invention, anti-idiotype antibodies that selectively bind to the TgAMA-1 binding polypeptides are provided.

According to yet another aspect of the invention, methods for treating a toxoplasma infection are provided. The methods include administering to a subject in need of such treatment, an effective amount of the foregoing TgAMA-1 binding polypeptides to treat the toxoplasma infection. In some embodiments, the TgAMA-1 binding polypeptide blocks the entry of *Toxoplasma* parasite into a cell. In some embodiments, the subject is a mammal. In certain embodiments, the subject is a human.

According to yet another aspect of the invention, methods for reducing the likelihood of a toxoplasma infection are provided. The methods include administering to a subject in need of such treatment, an effective amount of a foregoing TgAMA-1 binding polypeptide to reduce the likelihood of toxoplasma infection. In some embodiments, the TgAMA-1 binding polypeptide blocks the entry of Toxoplasma parasite into a cell. In some embodiments, the subject is a mammal. In certain embodiments, the subject is a human.

DETAILED DESCRIPTION

The invention relates in some aspects to a *Toxoplasma gondii* tachyzoite protein termed TgAMA-1. TgAMA-1 is relatively homologous to the extensively studied apical membrane antigen-1 (AMA-1) family of proteins of malaria parasites. In animal models of malaria, passive immunization with polyclonal antibodies against AMA-1, or immunization with native or recombinant renatured AMA-1, protect against parasite challenge; AMA-1 is currently under investigation as a vaccine candidate for human malaria. The antigenicity of malarial AMA-1 resides in its extracellular domain, with which TgAMA-1 shows a high degree of structural conservation. The present invention relates to the use of recombinant TgAMA-1 and its extracellular domain as vaccines for toxoplasmosis. The efficacy of TgAMA-1 as a vaccine is readily confirmed by administering TgAMA-1 and/or vaccine formulations comprising TgAMA-1 to test animals, such as mice. Cats and sheep (important animal reservoirs of Toxoplasmosis) are also readily tested to confirm the vaccine potential of TgAMA-1, as well as ultimately, humans.

As used herein, the term "TgAMA-1" means human *Toxoplasma gondii* apical membrane antigen-1. As used herein the term TgAMA-1 molecules includes TgAMA-1 polypeptides, TgAMA-1 nucleic acids, and polypeptides, such as antibodies, that bind to TgAMA-1 polypeptides described herein.

As used herein a "subject" shall mean a human or vertebrate animal including but not limited to a dog, cat, horse, cow, pig, sheep, goat, non-human primate (e.g. monkey), rabbit, rat, mouse, and bird. The term "subject" also includes cells collected from a human or animal, for example, blood collected for purposes such as, but not limited to, transfusions.

As used herein, the term "cell" means a cell capable of being infected by, or suspected of being exposed to Toxoplasma. This may include cells from a subject and cells grown in culture. In some embodiments, a cell may be a control cell, which has not been exposed to toxoplasma. Cell types may include, but are not limited to, neuronal cells, ocular cells, erythrocytes, and intestinal cells.

As used herein, the terms "toxoplasma infection", and "toxoplasmosis" refer to infection by all members of the genus *Toxoplasma*. The application of the invention is described in many cases with reference to *Toxoplasma gondii* parasites, and is intended to include application of the methods to all strains *Toxoplasma gondii*. The methods of the invention are also envisioned to apply to treatment of toxoplasma parasite infections that result from other toxoplasma species.

Particularly important subjects to which the present invention can be applied are subjects having been or suspected of having been exposed to toxoplasma, which includes subjects diagnosed with infection, exhibiting symptoms of infection, or having known or probable risk of exposure to toxoplasma infection.

A subject may or may not exhibit symptoms of infection such as fever, swollen lymph glands, muscle aches, and pains. Methods to diagnose symptomatic and asymptomatic toxoplasma infection are known to those of ordinary skill in the medical arts and include, but are not limited to, blood tests for antibodies to the toxoplasma parasite. Brain scans by computerized tomography (CT scan) or magnetic resonance imaging (MRI scan) may also be used in the diagnosis of toxoplasma infection.

Treatment as it relates to the invention may be prophylactic or therapeutic. Prophylactic and therapeutic treatment may involve administering a vaccine to induce/augment an immunoprotective response, or a polypeptide such as an antibody that binds TgAMA-1, to interfere with the toxoplasma parasite in the subject. Thus, in an important embodiment, the antibody to TgAMA-1 is administered to inhibit infection in a subject. As used herein, the term "reduce likelihood of infection" means to reduce or lower the level of entry into cells by the toxoplasma parasite. To "inhibit" or "block" may also mean to prevent entry into the cells by toxoplasma, but it is not necessary to prevent all entry to lessen or prevent the manifestation of disease.

As used herein the term "TgAMA-1 polypeptides" means the polypeptide set forth as SEQ ID NO: 1, variants of the polypeptide set forth as SEQ ID NO: 1, and fragments of the polypeptide set forth as SEQ ID NO: 1. As noted above, the invention provides isolated TgAMA-1 polypeptides and TgAMA-1 binding polypeptides, such as antibodies, that bind to TgAMA-1 polypeptides. The invention also embraces functional variants, such as fragments, of the TgAMA-1 polypeptides. As used herein, a "functional variant" or "variant" TgAMA-1 polypeptide is a molecule that contains one or more modifications to the primary amino acid sequence of the TgAMA-1 polypeptide and retains the antigenic function of TgAMA-1. Modifications that create a TgAMA-1 polypeptide functional variant can be made, for example, to enhance a property of an TgAMA-1 polypeptide, such as peptide stability in an expression system or the antigenicity of the TgAMA-1 protein; or to provide a novel activity or property to a TgAMA-1 polypeptide, for example, to enhance detection. Modifications to a TgAMA-1 polypeptide can be made to a nucleic acid that encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, substitution of one amino acid for another and the like. Modifications also embrace fusion proteins comprising all or part of the TgAMA-1 polypeptide amino acid sequence.

The amino acid sequence of polypeptides may be of natural or non-natural origin, that is, they may comprise a TgAMA-1 polypeptide molecule or may comprise a modified sequence as long as the amino acid sequence retains the antigenic property of TgAMA-1. For example, TgAMa-1 polypeptides in this context may be fusion proteins of a TgAMA-1 polypeptide and unrelated amino acid sequences, synthetic peptides of amino acid sequences shown in SEQ ID NO: 1, peptides isolated from cultured cells that express TgAMA-1, and peptides coupled to nonpeptide molecules (for example in certain drug delivery systems, e.g., across a cell membrane, or detectable labels).

An example, although not intended to be limiting, of a method with which antigenicity of a TgAMA-1 polypeptide can be tested involves in vivo testing in mice. One test involves the ability to enhance an antibody response to an antigen component of the TgAMA-1 antigen and/or the delayed-type hypersensitive (DTH) response, measured by an increase in footpad swelling after inoculation in the footpad of the test animal. These measurements can then be compared to corresponding measurements in control animals. Serum samples may be drawn from the mice after the final inoculation (for example every one or two weeks after inoculation). Serum can be analyzed for antibodies against the antigen using known methods in the art, e.g., using an ELISA. DTH response to the antigen may be measured after the final inoculation (e.g. within 1–7 days). An increase in the serum titer of antibodies recognizing the antigen and or an increase in footpad swelling in the animals receiving the putative TgAMA-1 antigen as compared to the serum titer of the control animals, indicates that putative TgAMA-1 antigen is an antigenic TgAMA-1 polypeptide of the invention.

If a functional variant involves a change to an amino acid if SEQ ID NO: 1, the functional variant of the TgAMA-1 polypeptide may have conservative amino acid substitutions, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of SEQ ID NO: 1 rely upon the development of amino acid sequence motifs to which potential epitopes may be compared. (See, e.g., published PCT application of Strominger and Wucherpfennig (U.S./96/03182)). In general, these methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a TgAMA-1 peptide position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for the TgAMA-1 polypeptide functional variants can be developed by analysis of the antigenic regions of the TgAMA-1 polypeptide disclosed herein. By providing a detailed structural analysis of the residues involved in the antigenicity of the TgAMA-1 polypeptide disclosed herein, one of ordinary skill in the art is enabled to make predictions of sequence motifs for antigenic regions of the TgAMA-1 polypeptides.

Using these sequence motifs as search, evaluation, or design criteria, one of ordinary skill in the art is enabled to identify classes of peptides (functional variants of the TgAMA-1 polypeptide disclosed herein) which have a reasonable likelihood of being antigenic and/or to which binding polypeptides such as antibodies can be produced that inhibit parasite entry into cells. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease such as toxoplasma infection.

The ability of the variant TgAMA-1 polypeptides to inhibit toxoplasma parasite entry into cells, is determined according to standard procedures. For example, the variant polypeptide can be contacted with the parasite, and standard procedures may be used to determine whether the parasite is inhibited in its ability to enter cells.

Variant TgAMA-1 polypeptides include "fragments" of the polypeptide having SEQ ID NO: 1. As used herein, a fragment has one or more amino acids fewer than the polypeptide set forth as SEQ ID NO: 1. Those of ordinary skill in the art may apply no more than routine procedures to identify such fragments, in view of the disclosures provided herein.

Variants and fragments as well as TgAMA-1 binding peptides such as antibodies may be tested for their ability to inhibit Toxoplasma activity. One method for inhibiting activity is by inhibiting entry of toxoplasma into cells. The ability to inhibit entry of toxoplasma parasite into cells with a TgAMA-1 polypeptide or binding polypeptide can be assessed using routine screening assays, e.g. by determining the level of TgAMA-1 mediated entry of Toxoplasma parasite into cells with and without the presence of the polypeptide. The ability of a putative TgAMA-1 polypeptide or binding polypeptide to out-compete toxoplasma parasite entry into cells can be determined by comparing the binding of the parasite TgAMA-1 to the cell in the presence and absence of the putative TgAMA-1 polypeptide or binding polypeptide. By comparing putative TgAMA-1 polypeptides or other binding peptides with the peptide of SEQ ID NO: 1, additional polypeptides with increased parasite inhibiting properties can be identified.

Nucleic acid sequences that code for a TgAMA-1 polypeptide or binding polypeptides, including allelic variants, are also a part of the invention. As used herein, an "isolated TgAMA-1 nucleic acid molecule" is a nucleic acid molecule that encodes an antigenic TgAMA-I polypeptide. A TgAMA-1 nucleic acid molecule can be the nucleic acid molecule set forth as SEQ ID NO: 2 or can be a fragment thereof. The TgAMA-1 nucleic acid molecules of the invention can also be variants of the nucleotide sequence set forth as SEQ ID NO: 2. The invention also encompasses Watson-Crick complements of the foregoing TgAMA-1 nucleic acid molecules. The TgAMA-1 nucleic acids of the invention may encode fragments or variants of the polypeptide set forth as SEQ ID NO: 1. In some embodiments, the TgAMA-1 nucleic acids of the invention do not encode the entire TgAMA-1 polypeptide of SEQ ID NO: 1, but do include nucleotide sequences encoding the TgAMA-1 polypeptide fragments disclosed herein, or functional equivalents thereof.

In screening for nucleic acids that encode a TgAMA-1 polypeptide or binding polypeptide of the invention, nucleic acid hybridization such as a Southern blot or a Northern blot may be performed under high stringency conditions, together with a labeled probe, for example, a $^{32}P$ probe. The term "high stringency conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary high stringency conditions include hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH 7), 0.5% SDS, 2 mM EDTA). SSC is 0.15 M Sodium Chloride/0.015 M Sodium Citrate, pH 7; SDS is Sodium Dodecyl Sulphate; and EDTA is Ethylene diaminetetraacetic acid. After hybridization, the membrane upon which the DNA is transferred can be washed, for example, at 2×SSC at room temperature and then at 0.1–0.5×SSC/0.1×SDS at temperatures up to 68° C. After washing the membrane to which DNA encoding a TgAMA-1 immunogenic polypeptide is finally transferred, the membrane can be placed against X-ray film to detect the radioactive signal.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the TgAMA-1 polypeptide of the invention. The skilled artisan also is familiar with the methodology for screening cells and libraries for expression of such molecules which then are routinely isolated, followed by isolation of the pertinent nucleic acid molecule and sequencing.

The invention also includes the use of nucleic acid sequences which include alternative codons that encode the same amino acid residues of the TgAMA-1 polypeptide or binding polypeptide of the invention. For example, leucine residues can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the TgAMA-1 polypeptide include: GUA, GUC, GUG and GUU (valine codons); GGU, GGA, GGG, GGC (glycine codons); UAC and UAU (tyrosine codons). Other amino acid residues may be encoded similarly by multiple nucleotide sequences. Thus, the invention embraces degenerate nucleic acids that differ from the native TgAMA-1 polypeptide encoding nucleic acids in codon sequence due to the degeneracy of the genetic code.

The invention also provides modified nucleic acid molecules, which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two, or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

It will also be understood that the invention embraces the use of the sequences in expression vectors, as well as to transfect host cells and cell lines. A host cell, as used herein, is any cell capable of expressing a peptide in the presence of appropriate expression vectors. Host cells include but are not limited to prokaryotic (e.g., *E. coli*), or eukaryotic (e.g., CHO cells, COS cells, yeast expression systems and recombinant baculovirus expression in insect cells, plasmids in High Five™ Cells). Especially useful are insect cells as host cells for expression in the invention. An example of useful insect cells, although not intended to be limiting, are High Five™ insect cells (see Examples). Plants may also be used to express the TgAMA-1 vaccines of the invention. The expression vectors require that the pertinent sequence, i.e., those described supra, be operably linked to a promoter. Thus, the polypeptides of the invention may be produced in host cells and delivered to a subject.

Alternatively, the peptides may be produced in vivo following administration of an expression vector with the TgAMA-1 nucleic acid to a subject. Delivery of expression vectors encoding the TgAMA-1 sequences in vivo and/or in vitro can be via the use of nucleic acid delivery systems known in the art (see, e.g., Allsopp et al., *Eur. J. Immunol.* 26(8):1951–1959, 1996). Recombinant vectors including viruses selected from the group consisting of adenoviruses, adeno-associated viruses, poxviruses including vaccinia viruses and attenuated poxviruses such as NYVAC, Semliki Forest virus, Venezuelan equine encephalitis virus, retroviruses, Sindbis virus, and Ty virus-like particle, plasmids (e.g. "naked" DNA), bacteria (e.g. the bacterium Bacille Calmette Guerin, BCG), and the like can be used in such delivery. For example, the expression vectors can be administered in vivo to produce the antigen as a vaccine. Other viruses, expression vectors and the like which are useful in preparation of a vaccine antigen in vivo are known to one of ordinary skill in the art. Since nucleic acids have some adjuvant properties an antigen expressed in vivo from an expression vector may not require an additional adjuvant. One can test the TgAMA-1 molecule delivery systems in standard model systems such as mice to determine efficacy of the delivery system. The systems also can be tested in human clinical trials.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, bacteria and virus genomes as disclosed herein, such as adenovirus, poxvirus and BCG. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. As noted above, some nucleic acids express only fragments of TgAMA-1 polypeptides that include antigenic fragments.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a TgAMA-1 polypeptide of the invention. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus to express proteins for immunization is disclosed by Warnier et al., in intradermal injection in mice for immunization against P1A (*Int. J. Cancer*, 67:303–310, 1996).

The invention also embraces expression kits, which allow the artisan to prepare a desired expression vector or vectors. Such expression kits include at least separate portions of at least two of the previously discussed materials. Other components may be added, as desired.

In another aspect of the invention transgenic non-human animals comprising the expression vector of the invention are provided. Such transgenic animals are capable of expressing a variable level of TgAMA-1 polypeptide. In some embodiments, a mammal is genetically modified to produce TgAMA-1 in its milk Techniques for performing such genetic modifications are described in U.S. Pat. No. 6,013,857, issued Jan. 11, 2000 for :Transgenic Bovines and Milk from Transgenic Bovines." The genome of the transgenic animal is modified to comprise a transgene comprising a DNA sequence encoding TgAMA-1 operably linked to a mammary gland promoter. Expression of the DNA sequence results in the production of TgAMA-1 in the milk. TgAMA-1 may then be isolated from milk obtained from the transgenic mammal (e.g. using a column comprising an antibody which binds to TgAMA-1). The transgenic mammal is preferably a bovine species.

The invention also encompasses peptides that bind to TgAMA-1, refereed to herein as TgAMA-1 polypeptides or peptides. TgAMA-1 binding polypeptides include but are not limited to anti-TgAMA-1 antibodies including polyclonal and monoclonal antibodies, antibody fragments, and other non-antibody peptides. Antibodies useful in the methods of the invention include but are not limited to monoclonal antibody B3.90, which binds to TgAMA-1 and is described herein, and polyclonal antibodies such as UVT59, which is described herein.

The TgAMA-1 binding polypeptides (e.g. anti-TgAMA-1 antibodies) of the invention selectively bind to TgAMA-1 polypeptides and in some embodiments inhibit entry of *Toxoplasma gondii* or other toxoplasma parasite into cells. Such TgAMA-1 binding polypeptides are prepared by standard methods.

In view of the foregoing, the invention also permits the artisan to treat a subject having a toxoplasma infection or at risk of developing a toxoplasma infection. Treatments include administering TgAMA-1 polypeptides, optionally in the form of a vaccine or a TgAMA-1 binding polypeptide, including the anti-TgAMA-1 antibodies of the invention disclosed herein.

In certain embodiments, the TgAMA-1 polypeptides and anti-TgAMA-1 antibodies of the invention are used to produce antibodies ("anti-TgAMA-1 antibodies") using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980). See also, U.S. Pat. No. 5,101,017, issued Mar. 31, 1992 to Rubinstein, et al., entitled, "Antibodies for providing protein against P. vivax malaria infection," which also reports the preparation of anti-idiotypic antibodies for treating infectious disease. References that report vaccine approaches for treating malaria disease, which is also a parasitic infection, include: U.S. Pat. No. 6,066,623, issued to Hoffman, et al., entitled "Polynucleotide vaccine protective against malaria, methods of protection and vector for delivering polynucleotide vaccines"; and U.S. Pat. No. 6,120,770, issued to Adams et al., entitled "*Plasmodium* proteins useful for preparing vaccine compositions."

The antibodies of the present invention are prepared using any of a variety of methods, including administering the TgAMA-1 polypeptides of the invention, antibodies selective for the foregoing, and the like to an animal to induce monoclonal or polyclonal antibodies. The production of monoclonal antibodies is according to techniques well known in the art.

Non-limiting examples of supports for affinity-separation of antibodies, including monoclonals, include the following: activated Sepharose, activated cellulose and activated Sephadex. "Activated" refers to the creation, on the insoluble material, of reactive chemical groups that will form covalent linkages with the antibody molecules when incubated together under appropriate conditions. Typically, reactive groups are introduced into the insoluble substrate by the action of cyanogen bromide (CNBr) at high pH.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fe region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, there are complementary determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205. Accordingly, humanized anti-TgAMA-1 antibodies, particularly those that selectively bind to SEQ ID NO: 1, and the use of such antibodies (e.g., to provide passive immunity to a subject) are embraced with the inventions disclosed herein.

For example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies and human monoclonal antibodies, such as those produced by mice having functional TgAMA-1 loci.

Such antibodies also may be used to identify tissues expressing protein or to purify protein. Antibodies, also may be coupled to specific labeling agents for imaging or to anti-infectious agents, toxins such as ricin, other cytostatic or cytolytic drugs, and so forth, for therapeutic purposes.

The invention also involves the use of anti-idiotypic antibodies. By using monoclonal antibodies that interact with TgAMA-1 polypeptide, it is also possible to produce anti-idiotypic antibodies which can be used to screen other molecules to identify whether the other molecule has the same binding specificity as the monoclonal antibody. Such anti-idiotypic antibodies can be produced using well-known hybridoma techniques (Kohler and Milstein, *Nature*, 256:495, 1975). An anti-idiotypic antibody is an antibody which recognizes unique determinants present on the known monoclonal antibodies. These determinants are located in the hypervariable region of the antibody. It is this region which binds to a given epitope and, thus, is responsible for the specificity of the antibody. An anti-idiotypic antibody can be prepared by immunizing an animal with a monoclonal antibody. The immunized animal will recognize and respond to the idiotypic determinants of the immunizing monoclonal antibodies and produce an antibody to these idiotypic determinants. By using the anti-idiotypic antibodies of the immunized animal, which are specific for the monoclonal antibodies of the invention, it is possible to identify other clones with the same idiotype as the monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, intravenous, intraperitoneal, intramuscular, intranasal, intracavity, subcutaneous, intradermal, or transdermal.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention involves the use of various materials disclosed herein to "immunize" subjects or as "vaccines." A "vaccine" as used herein is an antigen in a pharmaceutical formulation and optionally includes an adjuvant. As used herein, "immunization" or "vaccination" means increasing or activating an immune response against an antigen. It does not require elimination or eradication of a condition but rather contemplates the clinically favorable enhancement of an immune response toward an antigen. Generally accepted animal models can be used for testing of immunization against toxoplasma using a toxoplasma antigen polypeptide or nucleic acid. For example, toxoplasma parasite can be introduced into a mouse to create the disease, and one or more toxoplasma antigen can be delivered by the methods described herein. The effect on the toxoplasma disorder can be assessed as a measure of the effectiveness of the toxoplasma antigen immunization. Of course, testing of the foregoing animal model using more conventional methods for immunization include the administration of one or more toxoplasma antigen polypeptides or peptides derived therefrom, optionally combined with one or more adjuvants and/or cytokines to boost the immune response. Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more TgAMA-1 polypeptides are administered optionally with one or more adjuvants to induce an immune response or to increase an immune response. An adjuvant is a substance incorporated into or administered with antigen which potentiates the immune response. Adjuvants may include, but are not limited to: mineral gels, e.g., aluminum hydroxide;

surface active substances such as lysolecithin, pluronic polyols; polyanions; peptides; alum, MDP, N-acetyl-muramyl-L-threonyl-D-isoglutamine (thr-MDP), N-acetyl-nor-muramyl-L-analyl-D-isoglutamine, and N-acetylmuramy-L-alanyl-D-isoglutaminyl-L-analanine-2-(1'-2'dipalmitoyl-sn-glycero-3-hydroxyphosphroyloxy)-ethylamine, monophosphoryl lipid A; saponins (QS21; DQS21); QS-7, QS-17, QS-18, and QS-L1; incomplete Freund's adjuvant; complete Freund's adjuvant; montanide; vitamin E, oil emulsions, and various water-in-oil emulsions prepared from biodegradable oils such as squalene and/or tocopherol.

Adjuvants may enhance the immunological response by providing a reservoir of antigen (extracellularly or within macrophages), activating macrophages and stimulating specific sets of lymphocytes. Adjuvants of many kinds are well known in the art.

In some embodiments, the polypeptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

In some embodiments of the invention, the vaccine is a proteosome vaccine. Proteosomes are useful for immunopotentiation by rendering peptides immunogenic and enhancing the immunostimulating properties of larger peptides, proteins, and protein fragments. Methods for preparing proteosomes include, but are not limited to, preparation from meningococci, as described in U.S. Pat. No. 5,726,292, the contents of which is hereby incorporated in its entirety.

The preparations of the invention are administered in effective amounts. An effective amount is that amount of a pharmaceutical preparation that alone, or together with further doses, stimulates the desired response. In the case of treating an infectious disease such as toxoplasma, the desired response is inhibiting the onset, stage or progression of the disease or infection. This may involve only slowing the progression of the disease temporarily, although more preferably, it involves halting the progression of the disease permanently, or preventing infection.

The TgAMA-1 molecule dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

In one embodiment, the therapeutically effective amount of the TgAMA-1 molecule is that amount effective to inhibit toxoplasma entry into cells. Such inhibition can be determined using standard assays as described above. In other embodiments a therapeutically effective amount is that amount effective to induce an immune response against the parasite. Measurements of acute toxoplasma infection, including isolation of the parasite from either blood or other body fluids after subinoculation of the body fluid into the peritoneal cavity of mice can be used to assess the levels of parasites remaining in the blood after exposure. (see Harrison's Principles of Internal Medicine, 14/e, McGraw Hill Companies, New York, 1998). If no parasites are found in the mouse's peritoneal fluid, its anti-*Toxoplasma* serum titer can be evaluated 4 to 6 weeks after inoculation. The presence of *Toxoplasma gondii* in a subject's body fluid represents an acute infection, and the presence of *Toxoplasma gondii* in tissue biopsies is an indication only of the presence of tissue cysts and not acute toxoplasmosis. (see Harrison's Principles of Internal Medicine, 14/e, McGraw Hill Companies, New York, 1998). Additional methods of diagnosis and assessment of chronic and acute toxoplasma infection are known to those of skill in the art.

In addition, diagnosis of an acute *Toxoplasma gondii* infection by detection of the simultaneous presence of IgG and IgM antibody to *Toxoplasma* in the subject's serum. The presence of circulating IgA suggests an acute infection. The Sabin-Feldman dye test, the indirect fluorescent antibody test, and the enzyme-linked immunosorbent assay (ELISA) all satisfactorily measure circulating IgG antibody to *Toxoplasma*. Positive IgG titers (>1:10) can be detected as early as 2 to 3 weeks after infection. These titers usually peak at 6 to 8 weeks and decline slowly to a new baseline level that persists for life. The methods currently available for this determination are the double-sandwich IgM-ELISA and the IgM-immunosorbent assay (IgM-ISAGA). The double-sandwich IgA-ELISA is more sensitive than the IgM-ELISA for detecting congenital infection in the fetus and newborn. (see Harrison's Principles of Internal Medicine, 14/e, McGraw Hill Companies, New York, 1998).

In addition to the diagnostic tests described above, clinical features of toxoplasma infection can be monitored for assessment of infection. Theses features include, but are not limited to: assessment of the presence of eye lesions, brain lesions, and brain inflammation. Such assessment can be with methods known to one of ordinary skill in the art, such as ophthalmologic testing, CSF evaluation, and radiologic studies. (see Harrison's Principles of Internal Medicine, 14/e, McGraw Hill Companies, New York, 1998).

These types of tests, as well as others known to those of ordinary skill in the medical arts, may be used to assess the toxoplasma infection status of a subject and to evaluate a therapeutically effective amount of TgAMA-1 molecule or TgAMA-1 binding polypeptides administered. A first determination of toxoplasma infection may be obtained using one of the methods described above, and a subsequent determination of infection can be done and a comparison of the infection levels may be used to assess the effectiveness of TgAMA-1 molecule or TgAMA-1 binding polypeptides administration as a prophylactic or a treatment of the toxoplasma infection. Absence of a toxoplasma infection may be an indication for prophylactic intervention by administering TgAMA-1 molecules or TgAMA-1 binding polypeptides to prevent toxoplasma infection.

The TgAMA-1 molecules and TgAMA-1 binding polypeptides may be administered alone, in combination with each other, and/or in combination with other antitoxoplasma drug therapies. Antitoxoplasma agents (for treatment and/or prophylaxis) that may be administered with TgAMA-1 molecules or TgAMA-1 binding polypeptides may include, but are not limited to: pyrimethamine plus either sulfadiazine or clindamycin; trimethoprim; protein synthesis inhibitors such as clindamycin, chlortetracycline, and azithromycin; purine synthesis inhibitors such as arprinocid; atovaquone; spiramycin plus prednisone; Dapsone (diaminodiphenyl sulfone); macrolides including roxithromycin, clarithromycin, and azithromycin; and phenytoin.

The above-described drug therapies are well known to those of ordinary skill in the art and are administered by modes known to those of skill in the art. The drug therapies are administered in amounts that are effective to achieve the physiological goals (to reduce toxoplasma infection, and/or reduce toxoplasma titer in a subject), in combination with the TgAMA-1 molecules of the invention. Thus, it is contemplated that the drug therapies may be administered in amounts which are not capable of preventing or reducing the physiological consequences of the toxoplasma infections when the drug therapies are administered alone, but which are capable of preventing or reducing the physiological consequences of toxoplasma infection when administered in combination with the TgAMA-1 molecules of the invention.

The vaccine formulations of the invention may be administered to confer immunity to a subject at risk of exposure to toxoplasma, which thereby prevents, reduces the severity of or delays the onset of a subsequent Toxoplasma infection. Alternatively, the vaccines may be administered during an ongoing Toxoplasma infection to improve the effectiveness of the host's response to the infections Toxoplasma organism.

The invention also provides a pharmaceutical kit comprising one or more containers comprising one or more of the TgAMA-1 molecules and/or antibodies of the invention and or formulations of the invention. The kit may also include instructions for the use of the one or more TgAMA-1 molecules and/or antibodies of the invention for the treatment of toxoplasma infection.

EXAMPLES

Example 1

Antibody Generation and Characterization of TgAMA-1

Procedure
Parasite Culture

*T. gondii* tachyzoites (RH strain, unless otherwise indicated) were cultured in human foreskin fibroblasts as previously described [5] and filtered through a 10 μm polycarbonate filter (Poretics, Livermore Calif.) prior to use.

Antibodies

MAbs: MAb B3.90 (against TgAMA-1) and A3.2 (against GRA8) were generated as described [3, 6] and purified by ion exchange and gel filtration chromatography [7]. Ascites fluid containing MAb 6D10 (against MIC2) was prepared as described [1]. Ascites fluid containing MAb Tg49 (against ROP1) was generously provided by Joseph Schwartzman (Dartmouth College, Hanover N.H.). MAb 40-1a (against *E. coli* β-galactosidase) was developed by J. R. Sanes and obtained from the Developmental Studies Hybridoma Bank (University of Iowa, Department of Biological Sciences, Iowa City Iowa) as a hybridoma supernatant.

Polyclonal antibody UVT59: A synthetic peptide corresponding to residues 496–515 of TgAMA-1 (acetyl-EFQSDRGARKKRPSDLMQEA amide (SEQ ID NO: 3)) was coupled to keyhole limpet hemocyanin using the Imject Maleimide Activated mcKLH Kit (Pierce, Rockford Ill.). The peptide-carrier conjugate was used to generate rabbit polyclonal antisera (Cocalico Biologicals Inc., Reamstown Pa.); serum titers were determined by western blot and immunofluorescence microscopy. Synthetic peptide coupled to agarose using the SulfoLink Kit (Pierce) was used to affinity purify AMA-1-specific antibody UVT59 from total serum as recommended by the manufacturer, except that 0.01 vol of stock protease inhibitors (aqueous stock contains 2 mg/ml aprotinin, 2 mg/ml leupeptin, 16 mg/ml benzamidine, and 5 mg/ml 4-(2-aminoethyl)-phenylsulfonylfluoride; DMSO stock contains 5 mg/ml pepstatin) were added to the serum before applying it to the peptide column.

Sodium Dodecyl Sulfate Polyacrylamide Gel Electrophoresis (SDS-PAGE) and Western Blotting.

Proteins were resolved by SDS-PAGE in the presence (reducing) or absence (non-reducing) of 5% (v/v) β-mercaptoethanol and western blotted as described[3], using MAb B3.90, MAb 6D10, MAb 40-1a and polyclonal serum UVT 59 at dilutions of 23.2 μg/ml, 1/5000 (v/v), 1/100 (v/v), and 1/10,000 (v/v), respectively. Where indicated, blots were stripped by sequential incubation in PBS (2 changes, 5 min each), 4% (w/v) trichloroacetic acid (2 changes, 10 min each), and PBS (2 changes, 5 min each). Stripped blots were either reblocked and probed with a different antibody or exposed directly to X-ray film.

Triton X-114 (TX-114) Phase Partitioning

TX-114 phase partitioning of total parasite extracts was carried out as previously described [6]. After partitioning, the detergent phase was diluted to the original extract volume ($4 \times 10^7$ parasite equivalents/ml) with 50 mM Tris-HCl, pH 7.4 and 100 mM NaCl, supplemented with 3.0 U/ml *Bacillus cereus* phosphatidylinositol-specific phospholipase C (PI-PLC; Molecular Probes, Eugene Oreg.) and sequentially incubated for 5 min on ice, 35 min at 37° C. and 5 min on ice. The PI-PLC-treated detergent phase was then subjected to 2 additional rounds of phase partitioning, and analyzed by SDS-PAGE/western blotting.

Immunoaffinity Purification and Sequence Analysis

MAb B3.90 was covalently cross-linked to Affi-Gel Protein A-conjugated agarose (BioRad, Hercules Calif.) as previously described [8]. Approximately 2.5 mg of IgG was coupled per 1 ml of resin. Parasites were washed twice in phosphate-buffered saline (PBS), pH 7.4 and extracted for 45 min on ice in EXTR buffer (0.5% [v/v] Triton X-100 (TX-100), 50 mM Tris, pH 7.4, 100 mM NaCl) supplemented with 0.01 volumes of the aqueous and DMSO protease inhibitor stocks. The extracts were centrifuged at 14,000×g for 5 min at 4° C. to remove insoluble material; the protein concentration of the supernatant was determined using the DC Protein Assay (BioRad). Extract (5 ml, 3.5 mg total protein) was added to 450 μL of antibody-conjugated beads (prewashed three times with EXTR buffer) and rotated gently for 2 h at 4° C., followed by 4 washes (batchwise) with EXTR buffer. Bound antigen was eluted from the washed beads using two sequential incubations with 400 μl of non-reducing SDS-PAGE sample buffer for 10 min at 100° C. The pooled eluate was concentrated 10-fold using a Centricon RC/YM-30 centrifugal filter device (30,000 MWCO; Millipore, Bedford Mass.) and subjected to SDS-PAGE. The gel was stained for 30 min with 0.1% (w/v) Coomassie R-250 in 50% (v/v) methanol, 10% (v/v) acetic acid and destained for 1 h in 10% (v/v) methanol and 7.5% (v/v) acetic acid. The purified antigen was cut out of the gel, digested with trypsin, and analyzed at the Harvard Microchemistry Facility (Cambridge Mass.) by microcapillary reverse-phase HPLC nano-electrospray tandem mass spectrometry ($\mu$LC/MS/MS) on a Finnigan LCQ quadropole ion trap mass spectrometer. The fragmentation spectra were correlated with known sequences using previously described algorithms [9, 10].

Immunofluorescence

Methanol fixation. Parasites were attached to the surface of glass coverslips using Cell Tack (Becton Dickinson, Bedford Mass.) as described [3]. They were washed twice with PBS, pH 7.4, at 4° C. and fixed in 100% methanol for 5 min at −20° C. All subsequent incubations were carried out at 4° C. The fixed parasites were washed 4 times in PBS, blocked for 10 min in PBS containing 0.5% (w/v) bovine serum albumin (PBS-BSA), and incubated for 45 min in primary antibody diluted in PBS-BSA as follows: B3.90, 11.5 $\mu$g/ml; A3.2, 0.5 $\mu$g/ml; 6D10, 1/50 (v/v); Tg49, 1/100 (v/v); affinity purified UVT59, 12.5 $\mu$g/ml. They were then washed 3 times with PBS, incubated for 30 min in PBS-BSA containing either 1.5 $\mu$g/ml Alexa546-conjugated goat anti-mouse IgG (Molecular Probes, Eugene Oreg.) or 0.9 $\mu$g/ml Alexa546-conjugated goat anti-rabbit IgG (Molecular Probes), and washed three times with PBS. For dual label immunofluorescence, parasites were then incubated for 45 min in PBS-BSA containing MAb B3.90 which had been directly conjugated to Alexa488 using an Alexa488 Protein Labeling kit (Molecular Probes). The labeled parasites were washed 5 times in PBS and mounted on glass slides for observation.

Formaldehyde/glutaraldehyde fixation. Samples were processed as above, except that the methanol fixation step was replaced by 30 min at 4° C. in 2.5% (v/v) formaldehyde, 0.025% (v/v) glutaraldehyde. Where indicated, samples were permeabilized by including 0.1% (v/v) TX-100 in the PBS-BSA block and in the primary antibody incubation.

Unfixed/unpermeabilized suspension assay. Tachyzoites were washed twice in PBS, pH 7.4 by centrifugation for 4 min at 1000×g (23° C.) and incubated for 10 min at 4° C. in PBS-BSA, followed by 1 hr at 4° C. in PBS-BSA containing primary antibody, diluted as above. The labeled cells were washed 3 times in PBS, post-fixed 25 min at 4° C. in PBS containing 2.5% (v/v) formaldehyde and 0.025% (v/v) glutaraldehyde, washed 3 times in PBS, incubated with fluorescently conjugated secondary antibody as above, washed 5 times in PBS and mounted on glass slides in PBS for observation.

Microscopy. Samples were observed on a Nikon Eclipse E400 fluorescence microscope using Nikon filter cube XF100 (excitation 455–495 nm, emission 515–560 nm) for Alexa488 and filter cube XF102 (excitation 535–590 nm, emission 605–710 nm) for Alexa546. No Alexa488 fluorescence was detectable using the XF102 filter, and no Alexa546 fluorescence was detectable using the XF100 filter. Digitized images were obtained using either a VE1000SIT camera (Dage-MTI, Michigan City Ind.) with an LG-3 framegrabber and Scion Image v1.6 software (Scion Corp., Frederick Md.) or a SpotRT monochrome camera driven by Spot v. 3.01 (AppleEvent) software (Diagnostic Instruments Inc., Sterling Heights Mich.).

Immunoelectron Microscopy

Cryoimmunoelectron microscopy was performed as previously described [6], using MAb B3.90 (25 ug/ml) as primary antibody. No immunogold labeling was observed when primary antibody was omitted.

Secretion Assays

Tachyzoites (2F strain, constitutively expressing cytoplasmic $\beta$-galactosidase [generous gift of David Sibley]) were washed twice in DMEM+20 mM HEPES, pH 7.0 (4 min, 1000×g, 23° C.), and resuspended in 4 ml polystyrene round bottom tubes at a concentration of 2×10$^8$ tachyzoites/ml. The suspension was incubated for various times at 37° C. or treated for 15 min at 23° C. with either 1.0% (v/v) DMSO or 20 $\mu$M BAPTA-AM (1.0% [v/v] DMSO final), followed by 2 min at 37° C. with 200 nM A23187 (1.0% [v/v] DMSO final) or 1.0% ethanol. Cells were pelleted (4 min, 1000×g, 4° C.) and dissolved in SDS-PAGE sample buffer. Supernatants were recentrifuged (4 min, 1000×g, 4° C.) and dissolved in sample buffer. The samples were incubated for 10 min at 100° C. and analyzed by SDS-PAGE/western blotting. Gels to be probed with either Mab B3.90 or antipeptide antiserum UVT59 were run under non-reducing conditions; blots to be probed with Mab 6D10 were run under reducing conditions. The extent of parasite lysis was determined by measuring the levels of $\beta$-galactosidase in the supernatant, as previously described [4].

Subcellular Fractionation

A subcellular fraction enriched in micronemes was prepared as described [2] except that the microneme fraction was extracted with 0.01% saponin to recover the micronemal contents.

Labeling Parasites with $^{125}$I-iodonaphthylene Azide ($^{125}$I-INA)

INA was synthesized from 5-aminonaphthalene-1-azide [11] and labeled with $^{125}$I (Lofstrand Laboratories, Gaithersburg, Md.) to a specific activity of ≈1 mCi/$\mu$mol. Filtered parasites from a freshly lysed monolayer of human foreskin fibroblasts were washed twice (1000×g, 4 min, 23° C.) with IM-PR (phenol-red deficient DMEM+20 mM HEPES, pH 7.0), and resuspended in IM-PR to a concentration of 2×10$^8$ tachyzoites/ml. Reduced glutathione was added to a concentration of 15 mM. All subsequent manipulations were performed in low light. $^{125}$I-INA (DMSO stock, ≈1 mCi/ml) was added to the parasite suspension to a final concentration of 1.0% v/v DMSO. The suspension was added to an equal vol of IM-PR (37° C.) containing 2.0% (v/v) ethanol in a 4 ml polystyrene round bottom tube. The cells were incubated for 2 min at 37° C., pelleted (4 min, 1000×g, 4° C.), resuspended in IM-PR, and irradiated for 5 min at 4° C. using a shortwave ultraviolet lamp (UVP Inc., San Gabriel Calif.; Model UV6-54, 254 nm) at a distance of 2 cm. The parasites were pelleted (14,000×g, 5 min) and extracted (1.4×10$^6$ tachyzoites/$\mu$l, 45 min, 4° C.) in 0.5% (v/v) TX-100, 50 mM Tris pH7.4, 100 mM NaCl, 2 mM EDTA supplemented with 0.01 volumes of the aqueous and DMSO protease inhibitor stocks. Affinity purified polyclonal antibody UVT59 was coupled to agarose beads and 36 $\mu$l of beads were used to immunoprecipitate TgAMA-1 from 75 $\mu$l of the TX-100 extract as described above. Immunoprecipitated proteins eluted from the beads in 36 of sample buffer were analyzed by SDS-PAGE under reducing conditions and western blotted with antipeptide antiserum as described above. The membrane was then stripped as described above and exposed to BioMax MS X-ray film (Eastman Kodak, Rochester N.Y.) at −70° C.

Results

Identification and Initial Characterization of TgAMA-1

In experiments designed to identify novel, non-GPI-linked apical or peripheral tachyzoite antigens [3, 6], a MAb (B3.90) was generated that reacts with a 63 kDa protein on western blots of total tachyzoite extracts, and shows both apical and peripheral localization by immunofluorescence (see below). MAb B3.90 recognizes a 63 kDa antigen on western blots of non-reduced tachyzoite extracts. No bands were detected when the samples were treated with β-mercaptoethanol prior to SDS-PAGE.

In TX-114 phase partitioning experiments, the 63 kDa antigen is recovered in the detergent phase both before and after treatment with PI-PLC, consistent with the behavior of a non-GPI-linked, transmembrane protein. For the TX-114 phase partitioning tachyzoites (Total) were extracted on ice in a buffer containing 0.5% (v/v) TX-114 and the cleared extract (TX-114 Soluble) was separated into aqueous (Aqueous I) and detergent (Detergent I) phases at 37° C. The detergent phase was incubated with PI-PLC and partitioned again into aqueous (AqueousII) and detergent (DetergentII) phases. Fractions were analyzed by SDS-PAGE/western blotting ($4\times10^5$ parasite equivalents loaded per lane); the 60 kDa region of a western blot was probed with MAb B3.90. SAG1, the major GPI-linked protein of the tachyzoite, quantitatively shifted from the Detergent I fraction to the Aqueous II fraction under these conditions, confirming the effectiveness of the PI-PLC treatment.

The 63 kDa antigen was purified by immunoaffinity chromatography using MAb B3.90. Tryptic peptides prepared from the purified protein were analyzed by tandem microcapillary reverse-phase HPLC/ion trap mass spectrometry. The resultant fragmentation spectra unambiguously identified the 63 kDa antigen as Genbank entry AF010264 (deposited by Hehl, Oretga-Barria and Boothroyd), the *Toxoplasma* homolog (TgAMA-1) of *Plasmodium* AMA-1. Multiple sequence alignment of TgAMA-1 with AMA-1 from the different *Plasmodium* species revealed significant homology across all species. Most strikingly, 12 of the 16 cysteines whose positions are invariant among *Plasmodium* species are also conserved in TgAMA-1. These cysteines are known to form intramolecular disulfide bridges in *Plasmodium* AMA-1 [12]. Other notable features in the TgAMA-1 primary sequence are a putative signal peptide, with a predicted cleavage site between residues 22 and 23 (ASG-LS), and a potential transmembrane domain between residues 457 and 476.

TgAMA-1 is a Microneme Protein

To localize TgAMA-1 in *T. gondii*, we performed dual label immunofluorescence microscopy on free tachyzoites using MAb B3.90 and antibodies against known microneme (MIC2), rhoptry (ROP1), or dense granule (GRA8) antigens. In permeabilized parasites, TgAMA-1 was found in a cap-like distribution at the apical end of the tachyzoite. This distribution is indistinguishable from that of MIC2, but distinctly different from that of GRA8 or ROP1, suggesting that TgAMA-1 resides in the micronemes of *T. gondii* tachyzoites. Immunoelectron microscopy with MAb B3.90 supports this conclusion, as does the enrichment of TgAMA-1 in a partially purified microneme fraction.

Proteolytic Processing and Secretion of TgAMA-1

Four of the five previously identified microneme proteins (MIC1, MIC2, MIC4, MIC5) are constitutively secreted from the tachyzoite at a low basal rate at 37° C. [2, 4, 13]. In the case of MIC2, secretion is coincident with specific proteolytic processing of the protein [14, 15]. To determine if TgAMA-1 behaves similarly, tachyzoites were incubated at 37° C. in culture medium for various times, the cells were centrifuged, and assayed by western blot to determine the amount of TgAMA-1 released into the supernatant vs. the amount retained in the cell pellet. A 53-kDa fragment of TgAMA-1 was found to be constitutively secreted into the supernatant in a time-dependent manner.

The amount of TgAMA-1 or MIC2 released from live parasites into the culture supernatant after 0 m, 10 m, 30 m, 60 m, or 120 m at 37° C. was determined by western blotting with either MAb B3.90 (TgAMA-1) or 6D10 (MIC2). The estimated molecular masses of the secreted and cellular forms of TgAMA-1 were 53 and 63 kDa, respectively. The estimated molecular masses of full-length and processed forms of MIC2 are 115 kDa and 95–100 kDa, respectively [14]. The amount of TgAMA-1 (MAb B3.90) or MIC2 (MAb 6D10) released into the culture supernatant after a 2 minute incubation at 37° C. in the presence of: DMSO (DMSO control) was determined; B-A23187 (A23187, following BAPTA-AM pretreatment); B-ETOH (ethanol, following BAPTA-AM pretreatment); A23187 (A23187, no BAPTA-AM pretreatment); or ETOH (ethanol, no BAPTA-AM pretreatment), were detected by western blotting.

The full-length 63 kDa form, but no detectable amount of the 53-kDa fragment, was found to remain associated with the cell pellet. More than 33% of the total TgAMA-1 was found to be secreted into the supernatant in the form of the 53-kDa fragment after 120 min at 37° C., as estimated by comparison to serial loadings of total parasite extracts. The extent of non-specific parasite lysis under these conditions was determined to be less than 2%, based on the release of soluble β-galactosidase [4]. Thus, TgAMA-1 appears to be constitutively processed and secreted from the parasite at 37° C.

The secretion of the previously identified MIC proteins (and processing of MIC2) is enhanced by treatments which elevate intracellular calcium, including incubation with ethanol or the calcium ionophore A23187 [4, 15]. The secretion of the 53-kDa fragment of TgAMA-1 was also found to be dramatically enhanced following a 2-min treatment with ethanol or ionophore A23187 this enhanced secretion was abrogated by pretreating the parasites with the membrane permeant calcium chelator, BAPTA-AM.

Localization and Secretion of the N- and C-terminal Fragments of TgAMA-1

While full-length TgAMA-1 requires detergent for its solubilization, the 53-kDa secreted form of the protein was recovered in the low speed supernatant in the secretion assays, in the absence of added detergent. To test the hypothesis that the secreted fragment represents 53-kDa of the protein N-terminal to the putative transmembrane domain and that MAb B3.90 reacts with an epitope within this portion of TgAMA-1, we generated a rabbit polyclonal antiserum against a synthetic peptide corresponding to 20 amino acids C-terminal to the transmembrane domain. The anti-peptide antibody was found to be highly specific, recognizing a major 63 kDa band on western blots of tachyzoite extracts run under non-reducing condition (67 kDa under reducing conditions) and a minor band of approximately 12 kDa. The anti-peptide antiserum UVT59 recognized a major antigen of 63 kDa, and a minor antigen of 12 kDa on western blots of non-reduced tachyzoite extracts. The 63 kDa UVT59-reactive band migrated at 67 kDa under reducing conditions. The 12 kDa band was not detected on identical blots probed with MAb B3.90. Proteins of 67 and 12 kDa were also immunoprecipitated with the anti-peptide antibody, and are labeled in intact parasites with the photo-activatable hydrophobic probe $^{125}$I-INA. Labeling of a protein with $^{125}$I-INA provides evidence that a portion of the protein is embedded within a lipid bilayer [11].

The immunofluorescence pattern seen with the anti-peptide antibody was different from that seen with MAb B3.90. In methanol-permeabilized parasites, both antibodies showed a strong concentration of TgAMA-1 at the apical end of the parasite, superimposed on a fainter peripheral distribution. A similar pattern was seen in parasites fixed with formaldehyde/glutaraldehyde and permeabilized with TX-100 using MAb B3.90, but under these fixation/permeabilization conditions the anti-peptide antibody labeled the periphery of the parasite with little concentration at the apical end. Most strikingly, 10–50% of live tachyzoites showed peripheral labeling of varying intensity with MAb B3.90, whereas no staining was seen with the anti-peptide antibody.

Taken together, these data suggest that TgAMA-1 is proteolytically processed into at least two fragments: a 53 kDa N-terminal fragment which is released from the parasite and contains the epitope for MAb B3.90, and a 12 kDa C-terminal fragment which is recognized by the anti-peptide antibody and which remains associated with the parasite, presumably via its transmembrane domain. Secretion assay results are consistent with this model: the anti-peptide antibody recognizes full length TgAMA-1 and the 12 kDa peptide in the cell pellet but detects nothing in the supernatant after either 60 minutes of constitutive secretion or 2 minutes of ethanol/A23187-induced secretion. No soluble fragments of TgAMA-1 were detected with antipeptide antibody UVT59 in secretion assays. Parasites were preincubated for 2 min with or without BAPTA-AM, followed by a 2 min incubation in the presence of 1% ethanol. TgAMA-1 released into the assay supernatant was detected by western blotting with MAb B3.90; the blot was then stripped and reprobed with anti-peptide antibody UVT59. Significant ethanol-induced secretion of the 53 kDa peptide was observed with MAb B3.90; neither this fragment nor any other was detected in the supernatant using antipeptide antibody UVT59.

Example 2

Expression of AMA-1 in High Five™ Insect Cells

Recombinant TgAMA-1 and various fragments of TgAMA-1 have been expressed in *E. coli*, but Western blotting with the conformation-sensitive MAb B3.90 suggested that these recombinant fragments were incorrectly folded. Proper folding of recombinant protein is more likely to be obtained in eukaryotic cell expression systems. To this end, we have recently expressed recombinant TgAMA-1 in insect cells. Using conventional molecular genetic techniques, *Toxoplasma* AMA-1coding sequence corresponding to the signal peptide, ectodomain, and the transmembrane domain (amino acid residues 1–473) was amplified from cDNA and ligated into pIZ/V5-His(Invitrogen) in frame with both V5 and His eptiope tags. PIZ/V5-His encodes a Zeocin™ resistance selectable marker gene and the promoter, OpIE2, which drives constitutive expression of the inserted gene. The construct was transformed into *E. coli* and plasmid DNA was isolated from antibiotic resistant colonies. The presence of AMA-1 in pIZ/V5-His was confirmed by PCR, restriction digest analysis and sequencing. High Five™ cells were transfected with pIZ/AMA-1/V5-His and stable expression was indicated by Zeocin™ resistance. Antibiotic-resistant insect cell lines were cloned either by limiting dilution or by aspirating foci; AMA-1 expression was assayed by indirect immunofluorescence microscopy using monoclonal antibody B3.90 and an Alexa 488-conjugated secondary antibody. Recombinant TgAMA-1 expression in insect cells was detected with mAb B3.90.

REFERENCES

References

[1] Wan K L, Carruthers V B, Sibley L D, Ajioka J W. Molecular characterisation of an expressed sequence tag locus of *Toxoplasma gondii* encoding the micronemal protein MIC2. Mol Biochem Parasitol 1997;84:203–14.

[2] Carruthers V C, Giddings O K, Sibley D L. Secretion of micronemal proteins is associated with *Toxoplasma* invasion of host cells. Cellular Microbiology 1999; 1:225–235.

[3] Ward G E, Carey K L. 96—Well Plates Providing High Optical Resolution for High-throughput, Immunofluorescence-based Screening of Monoclonal Antibodies Against *Toxoplasma gondii*. J. Immunol. Meth. 1999;230:11–18.

[4] Carruthers V B, Sibley L D. Mobilization of intracellular calcium stimulates microneme discharge in *Toxoplasma gondii*. Mol Microbiol 1999;31:421–8.

[5] Roos D S, Donald R G, Morrissette N S, Moulton A L. Molecular tools for genetic dissection of the protozoan parasite *Toxoplasma gondii* In: Methods in Cell Biology. 45, 1994; 27–63.

[6] Carey K L, Donahue C G, Ward G E. Identification and molecular characterization of GRA8, a novel, proline-rich, dense granule protein of *Toxoplasma gondii*. Mol Biochem Parasitol 2000;105:25–37.

[7] Church W R, Brown S A, Mason A B. Monoclonal antibodies to the amino- and carboxyl-terminal domains of ovotransferrin. Hybridoma 1988;7:471–84.

[8] Harlow E, Lane D. Antibodies: A Laboratory Manual, Cold Spring Harbor: Cold Spring Harbor Laboratory, 1988.

[9] Eng J K, McCormick A L, Yates J R I. An approach to correlate tandem mass spectral data of peptides with amino acid sequences in a protein database. Journal of the American Society of Mass Spectrometry 1994;5:976–989.

[10] Chittum H S, Lane W S, Carlson B A, Roller P P, Lung F D, Lee B J, Hatfield D L. Rabbit beta-globin is extended beyond its UGA stop codon by multiple suppressions and translational reading gaps. Biochemistry 1998;37:10866–70.

[11] Bercovici T, Gitler C. 5-[$^{125}$I]Iodonaphthyl azide, a reagent to determine the penetration of proteins into the lipid bilayer of biological membranes. Biochemistry 1978; 17:1484–9.

[12] Hodder A N, Crewther P E, Matthew M L, Reid G E, Moritz R L, Simpson R J, Anders R F. The disulfide bond structure of *Plasmodium* apical membrane antigen-1. J Biol Chem 1996;271:29446–52.

[13] Brydges S D, Sherman G D, Nockemarn S, Loyens A, Daubener W, Dubremetz J-F, Carruthers V B. Molecular Characterization of TgMIC5, a proteolytically processed antigen secreted from the micronemes of *Toxoplasma gondii*. Molecular and Biochemical Parasitology (in press).

[14] Carruthers V B, Sherman G D, Sibley L D. The *Toxoplasma* adhesive protein MIC2 is proteolytically processed at multiple sites by two parasite-derived proteases. Journal of Biological Chemistry 2000;275:14346–14353.

[15] Carruthers V B, Moreno S N, Sibley L D. Ethanol and acetaldehyde elevate intracellular [$Ca^{2+}$] and stimulate microneme discharge in *Toxoplasma gondii*. Biochem J 1999;342:379–86.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. An isolated TgAMA-1 polypeptide molecule consisting of the polypeptide sequence set forth as amino acids 23–456 of SEQ ID NO:1.

2. A fusion protein comprising the antigenic polypeptide of claim 1.

3. A composition comprising the isolated TgAMA-1 polypeptide of claim 1 and pharmaceutically acceptable carrier.

4. The composition of claim 3, wherein the composition is a proteosome.

5. The composition of claim 3, wherein the composition includes an adjuvant.

7. The TgAMA-1 binding polypeptide of claim 6, wherein the binding polypeptide is an antibody.

8. The TgAMA-1 binding polypeptide of claim 7, wherein the antibody specifically binds to a region of about 12 or more cysteine residues of the isolated polypeptide of claim 1.

9. TgAMA-1 binding polypeptide of claim 6, wherein the binding polypeptide blocks entry of *Toxoplasma* parasite into a cell.

* * * * *

UNITED STATES PATENT AND TRADEMARK OFFICE
CERTIFICATE OF CORRECTION

PATENT NO.    : 6,902,926 B1
DATED         : June 7, 2005
INVENTOR(S)   : Gary E. Ward et al.

It is certified that error appears in the above-identified patent and that said Letters Patent is hereby corrected as shown below:

Title page,
Item [75], Inventors, should read -- Gary E. Ward, Essex Junction, VT (CA); Carolyn G. Conant, San Francisco, CA (US); Brian Ward, Montreal (CA) --

Column 32,
Line 1 should read as shown below.
-- The TgAMA-1 binding polypeptide of claim 6, wherein the --

Signed and Sealed this

Ninth Day of August, 2005

JON W. DUDAS
*Director of the United States Patent and Trademark Office*

SEQUENCE LISTING

<160> NUMBER OF SEQ ID NOS: 3

<210> SEQ ID NO 1
<211> LENGTH: 541
<212> TYPE: PRT
<213> ORGANISM: toxoplasmosis gondii

<400> SEQUENCE: 1

```
Met Gly Leu Val Gly Val Gln Val Leu Leu Val Leu Val Ala Asp Cys
1               5                   10                  15

Thr Ile Phe Ala Ser Gly Leu Ser Ser Ser Thr Arg Ser Arg Glu Ser
            20                  25                  30

Gln Thr Leu Ser Ala Ser Thr Ser Gly Asn Pro Phe Gln Ala Asn Val
        35                  40                  45

Glu Met Lys Thr Phe Met Glu Arg Phe Asn Leu Thr His His His Gln
    50                  55                  60

Ser Gly Ile Tyr Val Asp Leu Gly Gln Asp Lys Glu Val Asp Gly Thr
65                  70                  75                  80

Leu Tyr Arg Glu Pro Ala Gly Leu Cys Pro Ile Trp Gly Lys His Ile
                85                  90                  95

Glu Leu Gln Gln Pro Asp Arg Leu Pro Tyr Arg Asn Asn Phe Leu Glu
            100                 105                 110

Asp Val Pro Thr Glu Lys Glu Tyr Lys Gln Ser Gly Asn Pro Leu Pro
        115                 120                 125

Gly Gly Phe Asn Leu Asn Phe Val Thr Pro Ser Gly Gln Arg Ile Ser
    130                 135                 140

Pro Phe Pro Met Glu Leu Leu Glu Lys Asn Ser Asn Ile Lys Ala Ser
145                 150                 155                 160

Thr Asp Leu Gly Arg Cys Ala Glu Phe Ala Phe Lys Thr Val Ala Met
                165                 170                 175

Asp Lys Asn Asn Lys Ala Thr Lys Tyr Arg Tyr Pro Phe Val Tyr Asp
            180                 185                 190

Ser Lys Arg Leu Cys His Ile Leu Tyr Val Ser Met Gln Leu Met
        195                 200                 205

Glu Gly Lys Lys Tyr Cys Ser Val Lys Gly Glu Pro Pro Asp Leu Thr
    210                 215                 220

Trp Tyr Cys Phe Lys Pro Arg Lys Ser Val Thr Glu Asn His His Leu
225                 230                 235                 240

Ile Tyr Gly Ser Ala Tyr Val Gly Glu Asn Pro Asp Ala Phe Ile Ser
                245                 250                 255

Lys Cys Pro Asn Gln Ala Leu Arg Gly Tyr Arg Phe Gly Val Trp Lys
            260                 265                 270

Lys Gly Arg Cys Leu Asp Tyr Thr Glu Leu Thr Asp Thr Val Ile Glu
        275                 280                 285

Arg Val Glu Ser Lys Ala Gln Cys Trp Val Lys Thr Phe Glu Asn Asp
    290                 295                 300

Gly Val Ala Ser Asp Gln Pro His Thr Tyr Pro Leu Thr Ser Gln Ala
305                 310                 315                 320
```

| | | | | | | | | | | | |
|---|---|---|---|---|---|---|---|---|---|---|---|
| Ser | Trp | Asn | Asp | Trp | Trp | Pro | Leu | His | Gln | Ser | Asp | Gln | Pro | His | Ser |
| | | | 325 | | | | 330 | | | | 335 |

Ser Trp Asn Asp Trp Trp Pro Leu His Gln Ser Asp Gln Pro His Ser
                  325                  330                  335

Gly Gly Val Gly Arg Asn Tyr Gly Phe Tyr Tyr Val Asp Thr Thr Gly
                340                  345                  350

Glu Gly Lys Cys Ala Leu Ser Asp Gln Val Pro Asp Cys Leu Val Ser
            355                  360                  365

Asp Ser Ala Ala Val Ser Tyr Thr Ala Ala Gly Ser Leu Ser Glu Glu
370                  375                  380

Thr Pro Asn Phe Ile Ile Pro Ser Asn Pro Ser Val Thr Pro Pro Thr
                390                  395                  400

Pro Glu Thr Ala Leu Gln Cys Thr Ala Asp Lys Phe Pro Asp Ser Phe
              405                  410                  415

Gly Ala Cys Asp Val Gln Ala Cys Lys Arg Gln Lys Thr Ser Cys Val
            420                  425                  430

Gly Gly Gln Ile Gln Ser Thr Ser Val Asp Cys Thr Ala Asp Glu Gln
            435                  440                  445

Asn Glu Cys Gly Ser Asn Thr Ala Leu Ile Ala Gly Leu Ala Val Gly
            450                  455                  460

Gly Val Leu Leu Leu Ala Leu Leu Gly Gly Gly Cys Tyr Phe Ala Lys
465                  470                  475                  480

Arg Leu Asp Arg Asn Lys Gly Val Gln Ala Ala His His Glu His Glu
              485                  490                  495

Phe Gln Ser Asp Arg Gly Ala Arg Lys Lys Arg Pro Ser Asp Leu Met
            500                  505                  510

Gln Glu Ala Glu Pro Ser Phe Trp Asp Glu Ala Glu Glu Asn Ile Glu
            515                  520                  525

Gln Asp Gly Glu Thr His Val Met Val Glu Gly Asp Tyr
            530                  535                  540

<210> SEQ ID NO 2
<211> LENGTH: 2507
<212> TYPE: DNA
<213> ORGANISM: toxoplasmosis gondii

<400> SEQUENCE: 2

```
ggtgagggag cgcggccata cagtcatcaa tcgaacactg agacgaagca catggggctc      60
gtgggcgtac aagttttgct ggttcttgtg gcggattgca ccatattcgc atcgggactc     120
agctcaagca caaggtctcg cgagtcgcag acgctgagtg ctagcacgtc ggggaatccc     180
tttcaggcaa atgtagagat gaaaaccttc atggaaagat tcaacctaac tcatcatcat     240
cagtctggta tttacgtcga ccttggacaa gacaaggaag ttgatggcac attataccgg     300
gagcctgcgg ggttgtgtcc catttgggga agcacatcg aactccagca gccggaccgg      360
cttccgtacc gtaacaactt cttggaagat gttccgactg aaaaagaata caaacagtca     420
gggaatcctt tgcccggagg cttcaacttg aatttcgtga cgcctagcgg gcagcgaatt     480
tcaccatttc cgatggaact tcttgaaaaa aatagcaaca tcaaggcgag tacggatctt     540
ggaggtgcg ccgagtttgc ctttaagacg gtcgctatgg ataaaaacaa taaggcgacg      600
aagtaccgtt acccatttgt ttatgactcc aagaagcgac tgtgccacat cctctacgta     660
tcgatgcagc tgatgcaggg taaaaagtac tgttcagtca gggcgaacc tccagatctc      720
acatggtatt gcttcaagcc ccgaaagagt gttacggaga tcatcatct catctacgga      780
tcggcctatg ttgagagaa cccagatgcg ttcatcagta aatgcccaaa tcaagctctt     840
cgcgggtaca ggttcggtgt ttggaagaaa ggccgttgcc tcgactacac tgaattgacc     900
```

-continued

```
gacactgtga tagaacgtgt tgagtcaaag gcacagtgct gggtgaaaac ctttgaaaac    960
gacggggtcg cgagtgacca acccatacg tatccactga cgtcgcaagc atcatggaac   1020
gattggtggc ctctccacca gagtgaccaa cctcactcag gtggcgttgg gcgtaattac   1080
ggtttctact acgtggacac gactggagag ggcaagtgtg cactctctga ccaggtaccc   1140
gactgcctgg tgtcggattc tgccgccgtg tcgtatacag cagcggggag tttgtctgaa   1200
gagacgccga atttcataat tccgtcaaat ccctctgtta ctccgccaac gcccgagacg   1260
gcacttcagt gcacggccga caagttcccc gactctttcg gtgcctgcga cgttcaagcc   1320
tgtaaaagac agaagacgtc ctgcgttggc ggacagattc aaagtactag cgtcgactgc   1380
accgcggacg aacaaaatga atgtggctct aacactgcgt tgatcgctgg actcgccgta   1440
ggagggggttc tgctgttggc tcttctagga ggaggctgct acttcgcgaa gaggttggac   1500
agaaacaaag gcgtccaggc ggctcatcat gaacatgagt ttcagtcaga cagaggtgct   1560
cgaaaaaaga ggccaagcga tctcatgcaa gaggctgaac cgtcgttttg ggatgaggca   1620
gaggagaaca ttgaacaaga tggggaaaca catgttatgg tcgaggggga ttactagagt   1680
cagaagaaac tgggtacagt tttcccctca gaatgcagtc gttcgagaac aagttttctc   1740
tttttgttgc cttgatcaac aggacagtat aagttgtcgg cacatcatgc gcacacatga   1800
acacatgtat actttgtctg cgtgccgagc tgctgtgtgt caccgaccgt ctgtggtctg   1860
cctgagccaa taaattattg caacggctgt ttttttatgg cagtgtcgtg tgttgggatt   1920
catgtgctta caaaggatgt cccgatgccc agcgtgcgca caaacgtgca tttttttata   1980
ttagcctagt aaattgattg agtgcctgtg cacttcgtcg attccaattc gacccattca   2040
ggaagggaa cgcggtcagt aaaatgccct gttgagtcgt ttttctgata ctgattttca   2100
tgcggaaagc gtagtcagtg ctaaatgtac catttggaat ttgtcgtagg tcgacacaaa   2160
cagttgtgat tacggttctc gacgctagtg cgccaaatga agctcgcgaa acaaggtgtg   2220
aaggcttgat atctgacaac gcagaacaac gcagccggtt agtaggttgc gcctgcccca   2280
gtgaaatcgt cagtgcttta ccgttttcat gtgcgtacca ccgaaggcgc ttccgtgttc   2340
tttcatggcg gctaggaaaa tctatggaag gttaaccttc cattaagggt cgggacgtgc   2400
gtaaccatgc acaagaacag cgattccgta gtgctgcgtc ttacgctgtt gacattatgt   2460
cgccaactac catatcgtgt taaacgtacg gaagaacgcc aaaaaaa             2507
```

<210> SEQ ID NO 3
<211> LENGTH: 20
<212> TYPE: PRT
<213> ORGANISM: Toxoplasma gondii

<400> SEQUENCE: 3

Glu Phe Gln Ser Asp Arg Gly Ala Arg Lys Lys Arg Pro Ser Asp Leu
1               5                   10                  15

Met Gln Glu Ala
            20